(12) United States Patent
Suorsa et al.

(10) Patent No.: US 6,315,732 B1
(45) Date of Patent: Nov. 13, 2001

(54) IMAGING CATHETER AND METHODS OF USE FOR ULTRASOUND-GUIDED ABLATION

(75) Inventors: Veijo T. Suorsa, Sunnyvale; W. Martin Belef, San Jose; Niyazi Beyhan, Santa Clara; Donald S. Mamayek, Mountain View, all of CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/357,378

(22) Filed: Jul. 20, 1999

(51) Int. Cl.$^7$ ........................................................ A61B 8/00
(52) U.S. Cl. .................................... 600/466; 600/467
(58) Field of Search .................................. 600/459, 460, 600/461, 462, 463, 466, 467, 488

(56) References Cited

U.S. PATENT DOCUMENTS

| | | | |
|---|---|---|---|
| 4,706,681 | 11/1987 | Breyer et al. | 128/642 |
| 4,917,097 | 4/1990 | Proudian et al. | 128/662.06 |
| 4,998,933 | 3/1991 | Eggers et al. | 606/41 |
| 5,178,620 | 1/1993 | Eggers et al. | 606/41 |
| 5,228,442 | 7/1993 | Imran | 128/642 |
| 5,295,484 | 3/1994 | Marcus et al. | 128/660.03 |
| 5,385,148 | 1/1995 | Lesh et al. | 128/662.06 |
| 5,409,000 | 4/1995 | Imran | 128/642 |
| 5,419,767 | 5/1995 | Eggers | 604/114 |
| 5,456,259 | * 10/1995 | Barlow et al. | 600/459 |
| 5,571,088 | 11/1996 | Lennox et al. | 604/96 |
| 5,590,659 | 1/1997 | Hamilton et al. | 128/661.01 |
| 5,606,975 | * 3/1997 | Liang et al. | 600/462 |
| 5,630,837 | 5/1997 | Crowley | 601/2 |
| 5,640,371 | 6/1997 | Schmidt et al. | 367/153 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,713,363 | 2/1998 | Seward | 128/662.06 |
| 5,735,280 | 4/1998 | Sherman | 128/600.03 |
| 5,749,833 | 5/1998 | Hakki et al. | 600/380 |
| 5,752,518 | 5/1998 | McGee et al. | 128/662.06 |
| 5,769,847 | 6/1998 | Panescu et al. | 606/42 |
| 5,840,030 | 11/1998 | Ferek-Petric et al. | 600/439 |
| 5,846,204 | * 12/1998 | Solomon | 600/463 |
| 5,954,649 | 9/1999 | Chia et al. | 600/424 |
| 6,053,868 | 4/2000 | Geistert et al. | 600/439 |

FOREIGN PATENT DOCUMENTS

| | | | |
|---|---|---|---|
| WO 96/00036 | 1/1996 | (WO) | A61B/17/36 |
| WO 98/29032 | 7/1998 | (WO) | A61B/5/05 |

OTHER PUBLICATIONS

Zimmer, J. E., et al., The Feasibility of Using Ultrasound for Cardiac Ablation, IEEE Transactions on Biomedical Engineering, Sep., 1995, vol. 42, No. 9, pp. 891–897.

* cited by examiner

*Primary Examiner*—Marvin M. Lateef
*Assistant Examiner*—Maulin Patel
(74) *Attorney, Agent, or Firm*—Townsend and Townsend and Crew, LLP

(57) ABSTRACT

The present invention provides ultrasound imaging catheters, systems and methods for their use which will be particularly useful to monitor the positioning of ablation catheters. In one embodiment, an imaging catheter (10) includes a catheter body (11) having a distal end (12), a proximal end (14) and a longitudinal axis (16). A transducer (20) is rotatably coupled to the distal end. The transducer has an axis of rotation (24) that is at a non-zero angle relative to the catheter body longitudinal axis. Such a configuration provides an exemplary side-looking imaging catheter.

55 Claims, 8 Drawing Sheets

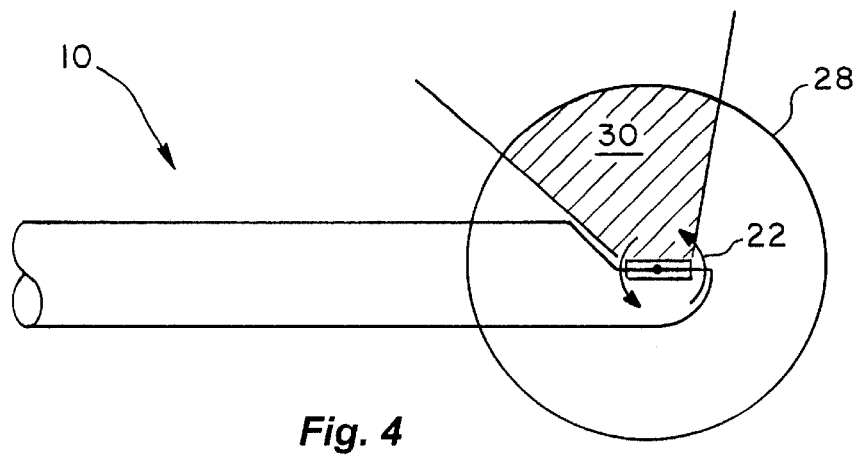
Fig. 4
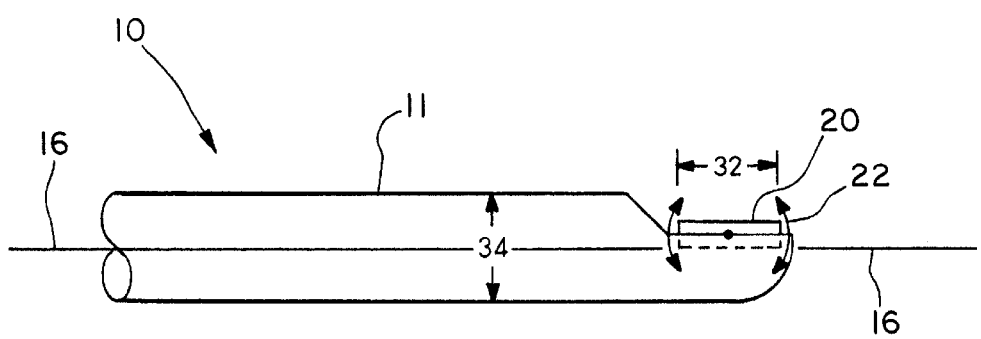
Fig. 5A
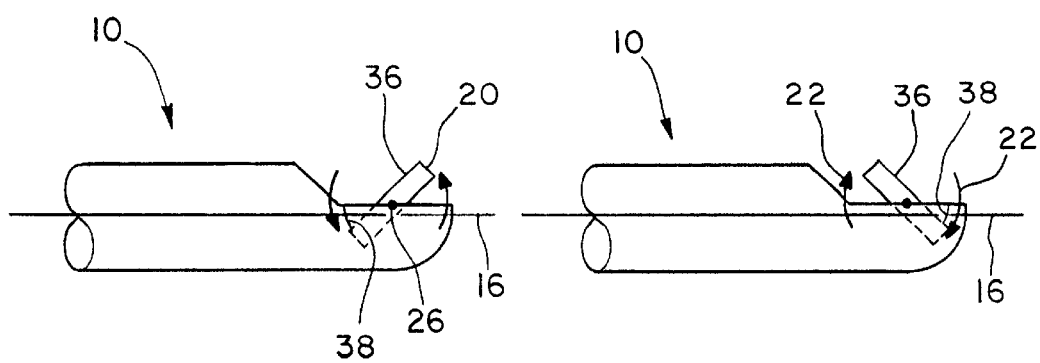
Fig. 5B          Fig. 5C

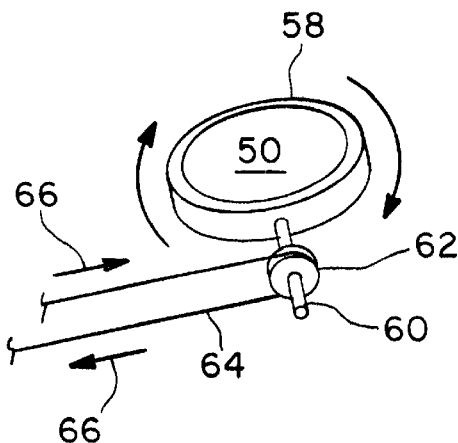
*Fig. 8A*
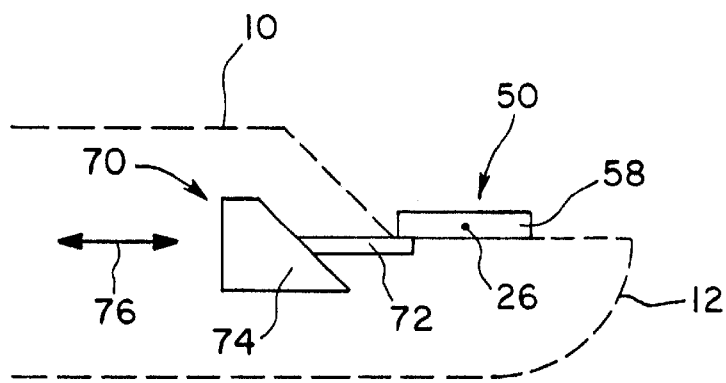
*Fig. 8B*
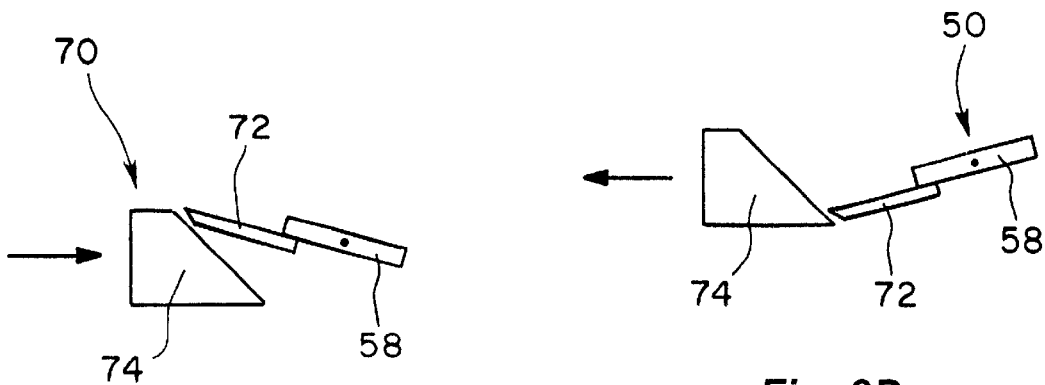
*Fig. 8C*
*Fig. 8D*

IMAGING CATHETER AND METHODS OF USE FOR ULTRASOUND-GUIDED ABLATION

BACKGROUND OF THE INVENTION

The invention relates generally to the field of ultrasound imaging, and in particular, to the imaging of body lumens with ultrasound imaging catheters.

Physicians make use of catheters today in medical procedures that are best performed by gaining access into interior regions of the body. For example, in electrophysiological therapy, ablation is used to treat cardiac rhythm disturbances. Such a therapy may be used, for example, to treat atrial fibrillation by forming long, thin lesions of different curvilinear shapes in heart tissue.

During these procedures, a physician steers a catheter through a vein or artery into the interior region of the heart that is to be treated. An ablation element carried on the distal end of the catheter is positioned near the tissue that is to be ablated. For such treatments, the delivery of ablating energy must be closely governed to avoid incidence of tissue damage and coagulum formation. Further, the ablation catheters must be precisely positioned adjacent to and preferably in contact with the tissue to be treated, to ensure the lesions are properly located.

Physicians and staff performing diagnostic and therapeutic procedures, such as electrophysiological therapy, typically require an imaging system to assist them in positioning the ablation catheter. Mini-transesophageal echocardiography (mini-TEE) probes are available, however, these probes must be swallowed or inserted down the patient's throat. Such probes are poorly tolerated by patients unless they are fully anesthetized. Further, these probes can be rather large (i.e., 20 French in diameter), use complex transducer configurations and are costly enough to discourage their disposal after a single use.

Alternatively, the use of ultrasound imaging systems, and in particular ultrasound imaging catheters, would be particularly useful in helping physicians monitor the positioning of ablation catheters. It is desirable, therefore, to have an ultrasound imaging catheter small enough to enter narrow and tortuous regions of the patient's vascular system. It also is desirable if such imaging systems were easy to operate and cost efficient to encourage their disposal after use.

SUMMARY OF THE INVENTION

The present invention provides ultrasound imaging catheters, systems and methods for their use. Catheters and systems of the present invention will be particularly useful to monitor the positioning of ablation catheters. Catheters and systems of the present invention provide a relatively simple and inexpensive apparatus compared to alternative monitoring techniques, such as mini-TEE probes.

In one embodiment, the present invention provides an imaging catheter comprising a catheter body having a distal end, a proximal end and a longitudinal axis. A transducer is rotatably coupled to the catheter body distal end. The transducer has an axis of rotation that is different from the catheter body longitudinal axis. Preferably, the transducer axis of rotation is generally perpendicular to the longitudinal axis. In this manner, the transducer rotates to produce images in an imaging plane that is generally parallel to the longitudinal axis. Such a configuration provides an exemplary side-looking imaging catheter.

In one aspect the catheter body has a diameter that is less than about 16 French. Catheters of such dimensions are sufficiently small enough to enter tortuous regions of a patient's vasculature. In another aspect, the transducer comprises PZT. The transducer also may comprise piezoplastics, piezocomposites, piezoceramics (e.g. PZT) and the like.

In one particular aspect, the transducer is rotatably coupled to the distal end to permit 360 degree rotation of the transducer about the transducer rotational axis relative to the distal end. In such an arrangement, the transducer is rotated to produce ultrasound images throughout an imaging plane without the need to rotate the catheter body. In another particular aspect, the transducer is rotatably coupled to the distal end to permit up to about 180 degree rotation of the transducer about the rotational axis relative to the distal end.

In one aspect, the transducer defines a face that is generally elliptical in shape, although other transducer shapes are possible within the scope of the present invention. In another aspect, the face has a major axis length that is greater than a diameter of the catheter body. In this manner, the transducer face major axis preferably is positioned generally parallel to the catheter body longitudinal axis. The transducer can be rotated up to about 180 degrees of rotation using a wiper-like or teeter-totter type of rotational movement.

In another aspect, the transducer comprises an annular array of transducer elements. In one aspect, the annular array defines a face that is generally elliptical in shape. Alternatively, the annular array defines a face that is generally circular in shape. The face may be generally flat or have a spherical or other curvature. Exemplary annular arrays for use in the present invention are further described in U.S. patent application Ser. No. 09/017,581, entitled "Annular Array Ultrasound Catheter," filed Feb. 3, 1998, and assigned to the assignee of the present invention, the complete disclosure of which is incorporated herein by reference.

In one aspect, the imaging catheter further includes a drive cable and a gear mechanism disposed within a working lumen of the catheter body. The drive cable is coupled to the transducer and to the gear mechanism. The drive cable and gear mechanism are adapted to rotate the transducer. In this manner, the drive cable and gear mechanism rotate the transducer, thereby eliminating the need to rotate the catheter body. In another aspect of the invention, the imaging catheter further includes a housing rotatably coupled to the distal end. The transducer is mounted within the housing. In such an embodiment, the transducer is rotated relative to the distal end by rotating the housing. Alternatively, the imaging catheter comprises a housing operably attached to the distal end with the transducer being rotatably coupled to the housing.

In another embodiment of the present invention, an imaging catheter is provided comprising a catheter body as previously described. The catheter further includes a plurality of transducer elements configured in an annular array. The annular array is rotatably coupled to the catheter body distal end, and has an axis of rotation that is at a non-zero angle relative to the catheter body longitudinal axis. Preferably, the annular array axis of rotation is generally perpendicular to the longitudinal axis.

In still another embodiment of the present invention, an imaging catheter includes a catheter body having a distal end, a proximal end and a longitudinal axis. A transducer is rotatably coupled to the distal end to permit up to about 180 degrees of rotation about an axis of rotation that is not coaxial with the longitudinal axis. More preferably, the transducer axis of rotation is generally perpendicular to the catheter body longitudinal axis. In one aspect, the transducer defines a face that is generally parallel to the longitudinal axis during a period of non-rotation. Preferably, the transducer is adapted to rotate so that the face creates an angle with the longitudinal axis that is between about +90° and about −90°.

The present invention further provides imaging catheter systems. In addition to an imaging catheter as previously described, the system includes a controller operably attached to the imaging catheter. The controller operates to display ultrasound images from signals received from the transducer and provides power to the imaging catheter. Such a system is particularly useful for the monitoring of accurate positioning of an ablation catheter prior to and/or during ablation.

The invention further provides exemplary methods of imaging a body lumen. One particular method includes the steps of providing an imaging catheter comprising a catheter body and a transducer coupled to the catheter body distal end. The method includes inserting the imaging catheter into a patient and positioning the transducer at a desired location within the patient. The transducer is rotated about an axis of rotation that is at a non-zero angle relative to the longitudinal axis. The method includes energizing the transducer, capturing a plurality of reflected signals, and producing an image of at least a portion of the desired location based on the reflected signals.

In one aspect of the method, the transducer is positioned at a desired location within a patient's heart. In this manner, the transducer can be positioned to monitor the positioning of an ablation catheter within a patient, such as within a patient's heart. In another aspect, the catheter body has a diameter that is less than about 16 French. In still another aspect of the method, a plurality of transducers configured in an annular array are provided. The annular array is rotatably coupled to the distal end and has an axis of rotation that is at an angle to the longitudinal axis.

In one aspect, the transducer is energized to project a plurality of ultrasound signals into an imaging plane. Preferably, the imaging plane is generally parallel to the longitudinal axis. In one aspect, the energizing and rotating steps are coordinated to project a plurality of ultrasound signals into a sector or portion of the imaging plane. In another aspect, the energizing and rotating steps are coordinated to project a plurality of ultrasound signals into a 360° sector of an imaging plane.

In one particular aspect of the method, an image of a portion of the imaging plane is produced. In still another aspect, the transducer is rotated through an angular displacement that is less than about 180°.

In one aspect of the method, the transducer defines a face that is generally parallel to the longitudinal axis during a period of non-rotation. The rotating step includes rotating the transducer so that the face creates an angle with the longitudinal axis that is between about +90° and about −90°.

In another exemplary method of imaging a body lumen according to the present invention, the method includes the step of providing an imaging catheter ostensibly as previously described with a transducer fixedly attached to the distal end. The method includes inserting the imaging catheter into a patient, positioning the transducer at a desired location within the patient, and energizing the transducer to project a plurality of ultrasound signals into a first sector of the desired location. The method includes capturing a plurality of reflected signals, producing an image of at least a portion of the first sector using the reflected signals and axially translating the transducer within the patient to a second sector of the desired location. The method includes repeating the energizing, capturing and producing steps for a second sector. More preferably, the transducer is axially translated a plurality of times to produce a plurality of images from a plurality of sectors of the desired location. In one aspect, a three-dimensional image is produced by combining the images of the first and second sectors.

In one aspect, the transducer is axially translated a specified distance by axially translating the proximal end the specified distance. In this manner, axial translation of the transducer can be controlled by axially translating the catheter proximal end maintained outside the patient's body.

In another aspect of the method, the energizing step projects a plurality of ultrasound signals into an imaging plane whereby the imaging plane is generally parallel to the longitudinal axis. In still another aspect, the providing step further includes providing a drive cable and a gear mechanism. The drive cable is coupled to the transducer and to the gear mechanism. The drive cable and gear mechanism are adapted to axially translate the transducer.

In another exemplary method of the present invention, an imaging catheter is provided as previously described. The catheter includes a housing proximal end that is coupled to a drive cable. The imaging catheter is inserted into a patient and the transducer is rotated by rotating the drive cable. The transducer is energized to project a first plurality of ultrasound signals into a first image plane. The method includes capturing a first plurality of reflected signals and producing a first image of at least a portion of the first image plane. The transducer is positioned at a desired location within the patient and the transducer is rotated relative to the distal end and to the drive cable. The method includes energizing the transducer to project a second plurality of ultrasound signals into a second plane, capturing a second plurality of reflected signals, and producing a second image of at least a portion of the second image plane. In this manner, the transducer produces images from two different image planes to help locate the desired location within the patient and to image the desired location.

In one aspect, the first image plane is generally perpendicular to the housing longitudinal axis and the second image plane is generally parallel to the housing longitudinal axis. In another aspect, images are produced of the first image plane until the transducer is positioned at the desired location within the patient.

In still another aspect, the same transducer projects signals into the first and second image planes. In a related aspect, the same transducer captures both the first and second plurality of ultrasound signals from the first and second image planes.

In still another exemplary method according to the present invention, an imaging catheter as previously described is provided and inserted into a patient. The method includes the steps of rotating the transducer relative to the distal end and relative to the drive cable, energizing the transducer to project a plurality of ultrasound signals from the transducer, and rotating the drive cable to rotate the transducer. The steps of rotating the transducer, energizing the transducer and rotating the drive cable occur simultaneously. As a result, the transducer projects a plurality of ultrasound signals into a three dimensional imaging region. The method includes capturing a plurality of reflected signals from the imaging region and producing a three-dimensional image of at least a portion of the imaging region. In this manner, the present invention provides imaging catheters and methods of imaging capable of producing three dimensional images.

In one aspect of the method, the transducer rotating step rotates the transducer through an angular displacement that is less than about 180 degrees. In another aspect, the drive cable rotating step rotates the drive cable 360 degrees to rotate the transducer 360 degrees. In this manner, the imaging region has a generally conical or hour-glass shape. Alternatively, the imaging region is generally cylindrical or spherical in shape.

In one particular aspect of the method, the transducer rotating step rotates the transducer at a first angular rate of rotation and the drive cable rotating step rotates the drive cable, and hence the transducer, at a second angular rate of rotation. In one aspect, the first angular rate of rotation is faster than the second angular rate of rotation.

Alternatively, the first angular rate of rotation is slower than the second angular rate of rotation.

In one aspect, the transducer rotating step rotates the transducer about an axis that is generally perpendicular to the longitudinal axis. Similarly, in another aspect the drive cable rotating step rotates the transducer about the longitudinal axis. In this manner, the transducer can image in more than one plane, and preferably in a three-dimensional imaging region.

Other features and advantages of the invention will appear from the following description in which the preferred embodiment has been set forth in detail in conjunction with the accompanying drawings.

BRIEF DESCRIPTION OF THE DRAWINGS

FIG. 4 depicts an imaging plane for the catheter depicted in FIG. 1;

FIGS. 5A–5C depict an alternative embodiment of an imaging catheter according to the present invention which provides up to about 180 degrees of transducer rotation;

FIG. 8A depicts a drive cable and gear mechanism for rotating a transducer;

FIGS. 8B–8D depict side views of a mechanism for rotating a transducer less than 360 degrees according to the present invention;

DESCRIPTION OF THE SPECIFIC EMBODIMENTS

Figure 1:
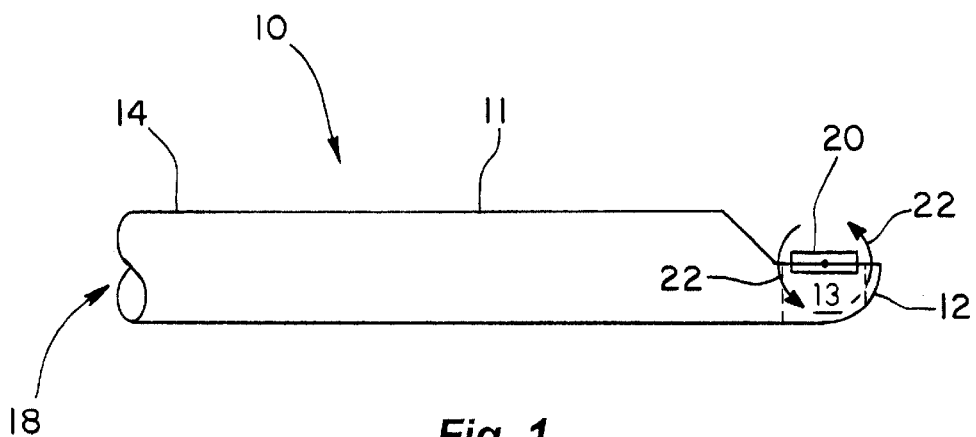
FIG. 1 provides an overall side view of an imaging catheter according to the present invention.
Figure 2:
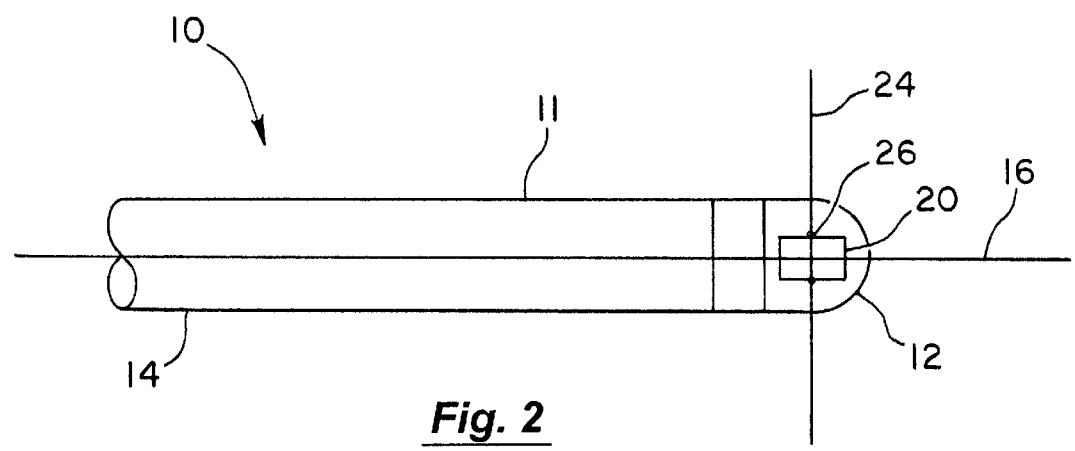
FIG. 2 provides an overall top view of the imaging catheter depicted in FIG. 1.

FIGS. 1 and 2 depict an imaging catheter 10 having a catheter body 11. Catheter body 11 has a distal end 12, a proximal end 14, and a longitudinal axis 16. A lumen 18 is provided within catheter body 11 and transducer 20 is rotatably coupled to distal end 12. Arrows 22 depict the rotation of transducer 20 with respect to distal end 12. While arrows 22 in FIG. 1 depict a counter-clockwise rotation, a clockwise rotation also may be used. Transducer 20 is rotatably coupled to catheter body 11 in a variety of manners. In one embodiment, transducer 20 is connected to distal end 12 using two rotatable attachment points 26 as shown in FIG. 2. Other attachment methods are within the scope of the present invention, some of which are discussed further in conjunction with FIG. 7.

Figure 3:
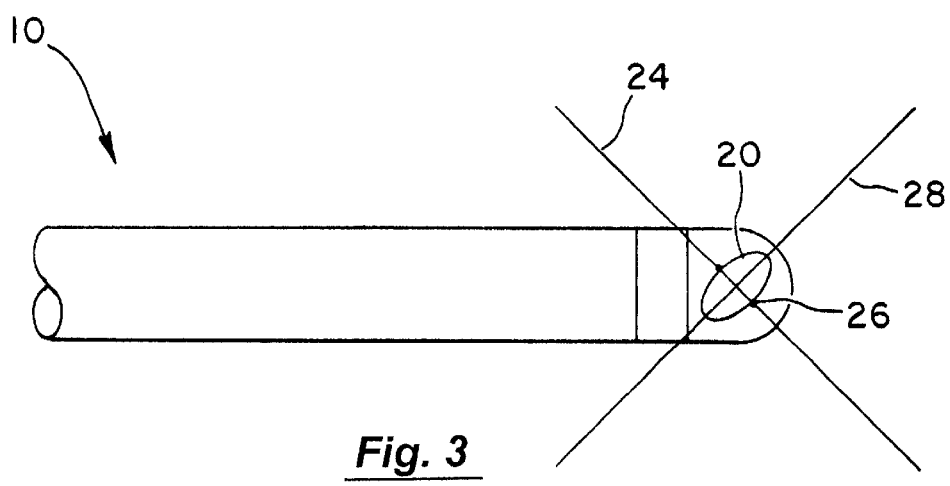
FIG. 3 provides an overall top view of an imaging catheter of the present invention showing the transducer element rotational axis positioned at an angle with respect to the longitudinal axis.

As best seen in FIGS. 2 and 3, transducer 20 rotates about an axis of rotation 24 that is not coaxial with the catheter body longitudinal axis 16. As shown in FIG. 2, transducer 20 has axis of rotation 24 that is generally perpendicular to longitudinal axis 16. Such an embodiment results in the image plane of transducer 20 being generally parallel to longitudinal axis 16. The image plane is the plane into which transducer 20 propagates ultrasound signals during operation, and from which transducer 20 receives signals reflected from tissue and the like. As shown in FIG. 3, in one embodiment transducer 20 has axis of rotation 24 that is out of alignment with longitudinal axis 16, but not perpendicular to axis 16. Such an embodiment will produce an image plane 28 that is at an angle with longitudinal axis 16.

As shown in FIG. 1, transducer 20 may be rotatably coupled to distal end 12 above a cavity 13. In one aspect, cavity 13 is filled with saline, or other coupling media. Alternatively, cavity 13 is at least partially filled with a material having a high absorbency to ultrasound signals. In this manner, ultrasound signals are propagated from transducer 20 in a direction generally opposite cavity 13. Transducer 20 may, but need not comprise a rectangular transducer element as depicted in FIG. 2. For example, FIG. 3 depicts transducer 20 as an elliptical or oval-shaped transducer element. Other shapes and configurations of transducer element 20 also are anticipated within the scope of the present invention. Further, transducer 20 may comprise a plurality of transducer elements, such as in the configuration described in conjunction with FIG. 6. Transducer 20 also may have a sound-attenuating backing material layer (not shown) operably attached to a transducer surface, and one or more matching layers (not shown) operably attached to an opposing transducer surface. Preferably, the matching layer(s)-transducer-backing material layer rotate together as a unit.

As depicted in FIG. 4, the rotation of transducer element 20 (shown by arrows 22) results in transducer 20 being capable of producing images in image plane 28. During operation, in one embodiment transducer 20 is rotated 360 degrees and energized to propagate ultrasound signals into image plane 28. Rotation of transducer 20 for 360 degrees may comprise continuous 360 degree rotation in one direction, or rotation in one direction (e.g., clockwise) for about 360 degrees followed by rotation in the other direction (e.g., counterclockwise) for about 360 degrees. One mechanism for providing such rotation is depicted in FIG. 8A. While the side view shown in FIG. 4 depicts a counter-clockwise rotation of transducer 20, a clockwise rotation also may be used. Transducer 20 can be energized to propagate ultrasound signals into about a 360° image plane 28. A portion of the ultrasound signals may be reflected or blocked by the catheter body. Hence not all signals will propagate into the patient's surrounding tissue. Alternatively, transducer 20 may be energized intermittently to propagate signals into a desired sector or region of image plane 28. FIG. 4 depicts transducer 20 propagating ultrasound signals into a sector 30 of image plane 28.

The coordination and production of ultrasound images of sector 30 can be accomplished in a variety of ways within the scope of the present invention. For example, transducer element 20 can be rotated and energized in a coordinated fashion to propagate ultrasound signals only into sector 30. Signals are reflected by a patient's tissues, fluids and the like, and the reflected signals are received by transducer 20. In one embodiment, one transducer 20 is used to transmit ultrasound signals and a second transducer 20 is used to receive reflected signals. The reflected signals can be used to produce an image of sector 30. Alternatively, transducer 20 can propagate ultrasound signals into a larger angular region of image plane 28 or into the entire image plane 28.

In such a situation, a controller or electronic processing equipment may produce ultrasound images only for desired sector 30 by, for example, using only those reflected signals received from sector 30. FIGS. 5A–5C depict an alternative embodiment of the present invention.

FIGS. 5A-C depict transducer element 20 rotatably coupled to catheter body 11 in a manner which provides less than 360° rotation of transducer 20. One mechanism for providing such rotation is depicted in FIGS. 8B–8D. Such an arrangement is particularly useful for allowing an aperture of transducer 20 to exceed the diameter 34 of catheter body 1. More specifically, FIG. 5A depicts transducer 20 having a span 32 that is greater than an inner diameter 34 of catheter body 11. Span 32 depends on the shape of transducer 20. For example, span 32 is the diameter of a circular-shaped transducer 20, is the major axis of an elliptical or oval transducer 20, and is the longest side of a rectangular-shaped transducer 20. In such an embodiment, transducer element 20 is not rotated in a 360° fashion, but instead is rotated as indicated by arrows 22 in an up and down, wiper-like or teeter-totter type fashion as best shown in FIGS. 5B and SC. During a period of nonrotation, a first face 36 of transducer 20 preferably is generally parallel to axis 16. During operation of imaging catheter 10, face 36 is rotated to produce an angle 38 with respect to axis 16 that varies between about +90° and about −90°. Transducer 20 rotates about rotating attachment points 26 to produce the rotational movement depicted by arrows 22. Catheter body diameter 34 preferably is less than about 16 French to permit its introduction into narrow, tortuous vasculatures.

Figure 6A:
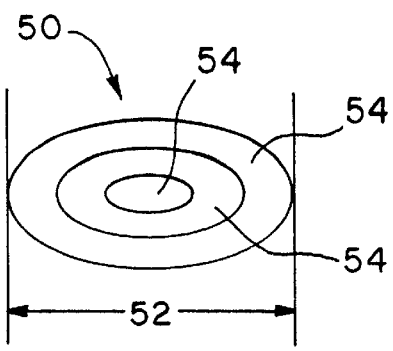
FIGS. 6A–6C depict top and side views of annular arrays for use with the present invention.
Figure 6B:
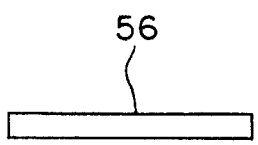
Figure 6C:
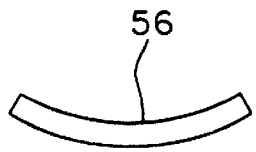

The embodiment described in conjunction with FIGS. 5A–C also would be useful in the event that transducer 20 is an annular array 50 of transducer elements. FIGS. 6A–6C depict alternative configurations of transducers for use in the present invention. While annular arrays are depicted, it will be appreciated by those skilled in the art that other arrays, including two-dimensional arrays and linear arrays, may be used within the scope of the present invention. FIG. 6A depicts an annular array 50 comprising a plurality of transducer elements 54. An annular array is defined as two or more generally concentric transducer elements surrounding a central point or axis. Annular arrays of the present invention are configured so that the transducer elements of the array propagate ultrasound signals in the same general direction. Annular arrays of the present invention further preferably have a central element to avoid a central blind spot in the array.

In one embodiment, array 50 has a major axis 52 that is longer than inner diameter 34 of catheter body 11. Such a configuration would be useful as described in conjunction with FIGS. 5A–5C. Preferably, insulating materials or kerfs (not shown) are provided between transducer elements 54 of array 50 to reduce or eliminate cross-talk between adjoining transducer elements 54. FIGS. 6B and 6C depict two possible configurations of a face 56 of annular array 50. FIG. 6B depicts a generally flat face 56 and FIG. 6C depicts face 56 having a spherical curvature. It will be appreciated by those skilled in the art that face 56, within the scope of the present invention, also may have a different curvature than shown in FIG. 6. For example, face 56 may have an elliptical or other focused curvature. Further, transducer 20 may be similarly shaped.

Figure 7A:
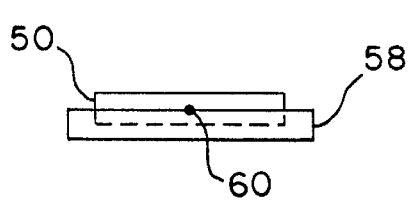
FIGS. 7A–7C depict a housing and transducer to be rotatably coupled to the catheter body.
Figure 7B:
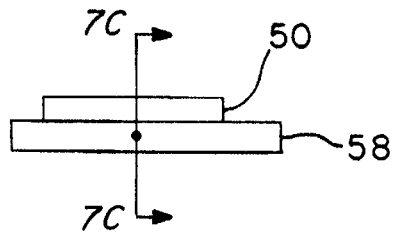
Figure 7C:
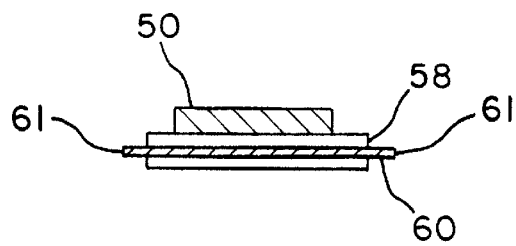

Turning now to FIG. 7A–7C, one manner of rotatably attaching transducer array 50 or transducer 20 to catheter body 11 according to the present invention will be described. As shown in FIG. 7A, array 50 is fixedly attached to a housing 58 having rotating attachment points 60. Rotating attachment points 60 then are rotatably attached to distal end 12 to allow housing 58 and array 50 to rotate about attachment points 60. While attachment points 60 are depicted in the approximate center of housing 58 or array 50, attachment points 60 also may be located off center. FIG. 7A depicts transducer array 50 partially disposed within housing 58 as indicated by dashed lines. FIG. 7B depicts array 50 operably attached to a surface of housing 58. Alternatively, array 50 may be fully disposed within a hole (not shown) within housing 58.

FIG. 7C depicts a cross-sectional view of housing 58 and array 50 depicted in FIG. 7B. FIG. 7C depicts rotating attachment point 60 as an axle or a rod extending through housing 58 (not cross-hatched for convenience of illustration). The ends of attachment points 60 are rotatably attached to distal end 12 to allow housing 58/array 50 to rotate about attachment points 60. For example, an end 61 of attachment point 60 can be inserted into holes, slots, grooves and the like, in distal end 12 of catheter body 11 to permit rotation. The configuration depicted in FIGS. 7A–7C may be used for rotation of array 50 (or transducer 20) 360 degrees (as in FIG. 4) or less than 360 degrees (as in FIGS. 5A–C).

FIG. 8A depicts an embodiment for rotating transducer array 50 about an axis that is not coaxial with longitudinal axis 16. As shown in FIG. 8A, attachment point 60 is rotatably coupled to housing 58 and a gear mechanism 62 is operably attached thereto. A drive cable 64 extends around gear mechanism 62. Arrows 66 indicate rotational movement of drive cable 64. Movement of drive cable 64 causes gear mechanism 62 to rotate which, in turn, causes the rotation of transducer array 50. While arrows 66 indicate a clockwise rotational movement in FIG. 8A, it will be appreciated that a counter-clockwise rotational movement also is within the scope of the present invention for both transducer 20 and array 50.

FIGS. 8B–8D depict a mechanism for rotating transducer array 50 or transducer 20 in a teeter-totter or wiper-like fashion in accordance with the present invention. Transducer array 50 is depicted in housing 58 coupled to distal end 12 of catheter 10. Attachment points 26 provide a position about which housing 58 rotates as previously described. As shown in FIG. 8B, a translation mechanism 70 is provided near distal end 12 to provide the teeter-totter motion of housing 58. Mechanism 70 comprises a support member 72 and a translation block 74. Axial movement of block 74, as shown by arrow 76, causes one end of support member 72 to slide up or down block 74. In one embodiment, a spring or other tension member (not shown) is coupled to support member 72 to bias support member 72 into block 74, thereby facilitating the sliding motion thereof as block 74 is axially translated. Support member 72 further is coupled to housing 58, and has sufficient stiffness to encourage rotation of housing 58 about points 26 as block 74 is translated. FIG. 8C depicts the translation of block 74 towards distal end 12, causing array 50 to rotate into a forward looking position. FIG. 8D depicts the translation of block 74 away from distal end 12, causing array 50 to rotate into a rearward looking position. By alternating the forward and rearward movements of block 74, array 50 undergoes a teeter-totter or wiper-like motion about the array 50 rotational axis defined by points 26.

The axial translation of block 74 may be accomplished in a number of ways. By way of example and not limitation, block 74 may be coupled to a small motor (not shown) in distal end 12 to provide the axial motion indicated by arrow 76. Block 74 further may be coupled to pair of orthogonal gears which translate a rotational motion, such as the rotation of a drive cable (not shown), into an axial motion of block 74. It will be appreciated by those skilled in the art that other methods of axially translating block 74 also may be used within the scope of the present invention.

Figure 9:
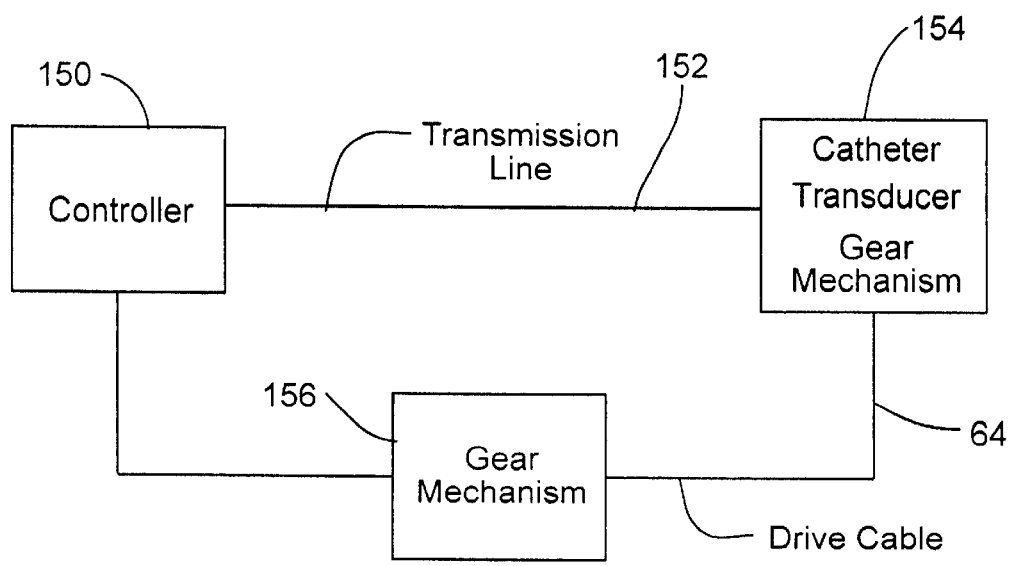
FIG. 9 depicts a schematic of an imaging catheter system according to the present invention.

FIG. 9 depicts a controller 150 operably attached to a gear mechanism 156 and a transmission line 152. Transmission line 152 is operably attached to catheter 154 as further described below. Catheter 154 is essentially the same as catheter 10 as previously described, including transducer 20 and a gear mechanism located at the catheter distal end, such as gear mechanism 62 described in conjunction with FIG. 8.

Catheter 154 is operably attached to gear mechanism 156 using drive cable 64. Drive cable 64 is operably attached to gear mechanism 62 in distal end 12 of catheter 10 as depicted, for example, in FIG. 8. Drive cable 64 is operably connected to gear mechanism 156 which provides the rotational movement of drive cable 64 as indicated by arrows 66 in FIG. 8. Single transducer catheters typically involve fixedly attaching a transducer to a distal end of a drive cable, and rotating the drive cable to rotate the transducer. Such an arrangement results in the transducer having an axis of rotation that is coaxial to the catheter body longitudinal axis. In the present invention, gear mechanism 156 is used to translate that typical rotational movement of a drive cable into a rotational movement of the transducer. It will be appreciated by those skilled in the art that gear mechanism 156 may comprise, for example, a pair of orthogonal gears to transfer rotational movement from one direction to another.

Transmission line 152 preferably extends from controller 150, through catheter lumen 18, and is adapted to be in electrical communication with transducer 20. In one embodiment, lumen 18 is contained within drive cable 64. For the embodiment depicted in FIGS. 5A–5C, transmission line 152 may be operably attached to transducer 20 or transducer array 50. For the embodiment described in FIG. 1, transducer 20 or array 50 is depicted being rotated 360 degrees. Transmission line 152 in one such embodiment is in communication with transducer 20 using slip rings (not shown), inductive coupling, flexible leads for embodiments having non-continuous 360 degree rotation, or the like.

Controller 150 includes electronics to provide power to imaging catheter 10. Controller 150 further includes image producing software and the like for displaying ultrasound images of desired regions within the patient's anatomy.

Figure 10A:
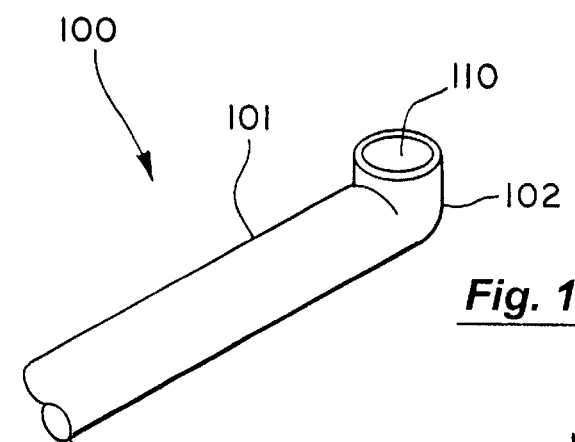
FIGS. 10A–10B depict an alternative embodiment of an imaging catheter according to the present invention.
Figure 10B:
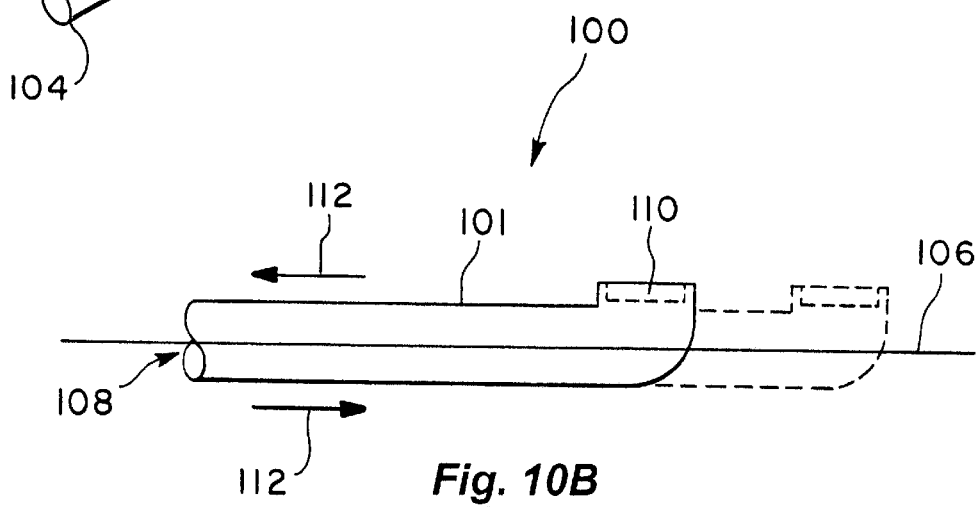

Turning now to FIG. 10, an alternative embodiment of the present invention will be described which makes use of controller 150 and gear mechanism 156 described in conjunction with FIGS. 8 and 9. More specifically, an imaging catheter 100 is provided having a catheter body 101 with a distal end 102 and a proximal end 104. A transducer 110 or an array of transducer elements are operably attached to distal end 102 of catheter body 101. Gear mechanism 156 is configured to provide a piston-like or forward and back motion of catheter 100 as depicted in FIG. 10B. The motion, as indicated by arrows 112, is generally parallel to the longitudinal axis 106 of catheter body 101. Transmission lines and drive cables (not shown) are disposed within a lumen 108 of catheter body to provide the piston-like motion. In one embodiment, proximal end 104 is coupled to a drive cable, and the transmission lines are disposed within a lumen within the drive cable.

Gear mechanism 156 (see FIG. 9), located outside the patient's body, is adapted to provide the piston-like movement shown by arrows 112. For example, proximal end 104 may be connected to gear mechanism 156, to provide movement shown by arrows 112. The extent of movement is controlled by controller 150, which operates to control gear mechanism 156. Alternatively, a physician may manually manipulate catheter 100 to produce axial movement of transducer 110 in the manner shown by arrows 112.

A method of using catheter 100 includes inserting catheter 100 into a patient and positioning transducer 110 at a desired location within the patient. Transducer 110 is energized to project a plurality of ultrasound signals into a first sector of the desired location. A plurality of reflected signals are captured, and an image of at least a portion of the desired location is produced using the reflected signals. Transducer 110 is axially translated to a second sector of the desired location to produce an image of the second sector in the same manner. As previously described, axial translation of transducer 110 can occur by a gear mechanism which provides a forward and back, piston-like movement. Alternatively, the physician can manually manipulate the catheter in an axial manner.

This embodiment will be particularly useful for producing three-dimensional images by combining the motion shown by arrows 112, with rotation of catheter 100 about longitudinal axis 106. As further described in conjunction with FIGS. 11A–11C, rotation of catheter 100 while projecting ultrasound signals from transducer 110 results in an image plane that is generally perpendicular to longitudinal axis 106. By simultaneously translating transducer 110 axially, such as shown by arrows 112, a three dimensional region is imaged.

Figure 11A:
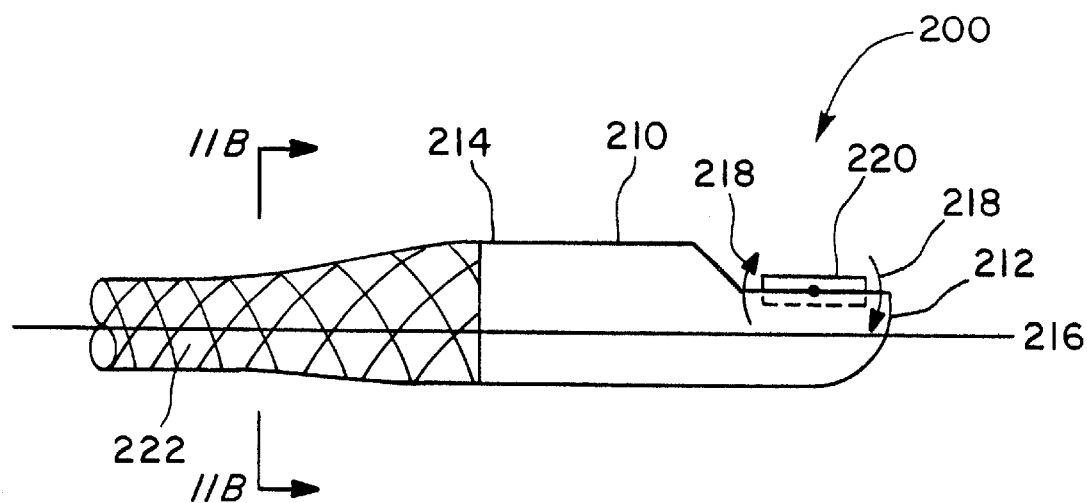
FIGS. 11A–11B depict still another embodiment of an imaging catheter according to the present invention.
Figure 11B:
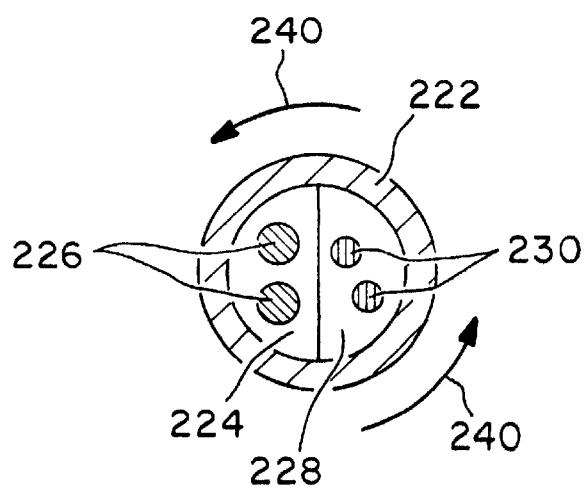

FIGS. 11A–11B depict an imaging catheter 200 according to an alternative embodiment of the present invention. Catheter 200 has a housing 210. Housing 210 has a distal end 212, a proximal end 214 and a longitudinal axis 216. A transducer 220 is rotatably attached to distal end 212 as described in conjunction with earlier Figures. Proximal end 214 is operably attached to a housing drive cable 222. Housing drive cable 222 may comprise, for example, stainless steel counterwound drive cables. Exemplary drive cables are described in U.S. patent application Ser. No. 09/017,578, entitled "Integrated Coaxial Transmission Line and Flexible Drive Cable," the complete disclosure of which is incorporated herein by reference. Catheter 200 may be disposed within a sheath (not shown), such as a polyethylene sheath.

In one embodiment, housing drive cable 222 has a first lumen 224 and a second lumen 228 as depicted in FIG. 11B. First lumen 224 contains a transducer drive cable 226, similar to drive cable 64 described in conjunction with FIG. 8. Transducer drive cable 226 operates to rotate transducer 220 relative to housing 210 as previously described and as shown by arrows 218. Second lumen 228 contains one or more transmission lines 230, to permit the transmission/receipt of signals to/from transducer 220. Housing drive cable 222 connects to proximal end 214 and rotates housing 210 as shown by arrows 240 so that housing 210 has an axis of rotation that is generally parallel to axis 216. It will be appreciated by those skilled in the art that arrows 218 and 240 can be used to indicate either clockwise or counterclockwise rotations.

Referring to FIGS. 11A–11B, a method of operating catheter 200 will be described. Catheter 200 is inserted into a patient and maneuvered to position transducer 220 at a desired location within the patient. To assist with this positioning step, housing drive cable 222 is rotated, which rotates housing 210 and transducer 220. Transducer 220 is energized to transmit ultrasound signals into an image plane, preferably a 360 degree image plane, that is generally perpendicular to axis 216. During the rotation of housing 210, transducer 220 is maintained generally stationary with respect to housing 210. Reflected signals are captured and transmitted to a controller, such as controller 150 described in conjunction with FIG. 9. The reflected signals are used to produce an image, which the operator or controller 150 can analyze to help determine the location of transducer 220 within the patient, for example by identifying known anatomical landmarks. This imaging mode can continue until transducer 220 reaches the desired location within the patient.

Once transducer 220 is positioned at the desired location, rotation of housing 210 ceases, and transducer 220 is rotated relative to housing 210 as described in conjunction with earlier Figures. For example, transducer drive cables 226 may be used to rotate transducer 220. In this second imaging mode, transducer 220 produces images in a second image plane. The second image plane may be generally parallel to axis 216 (see FIG. 2) or at an angle relative to axis 216 (see FIG. 3). Using the above-described method, transducer 220 is adapted to produce images in at least two different image planes.

Figure 11C:
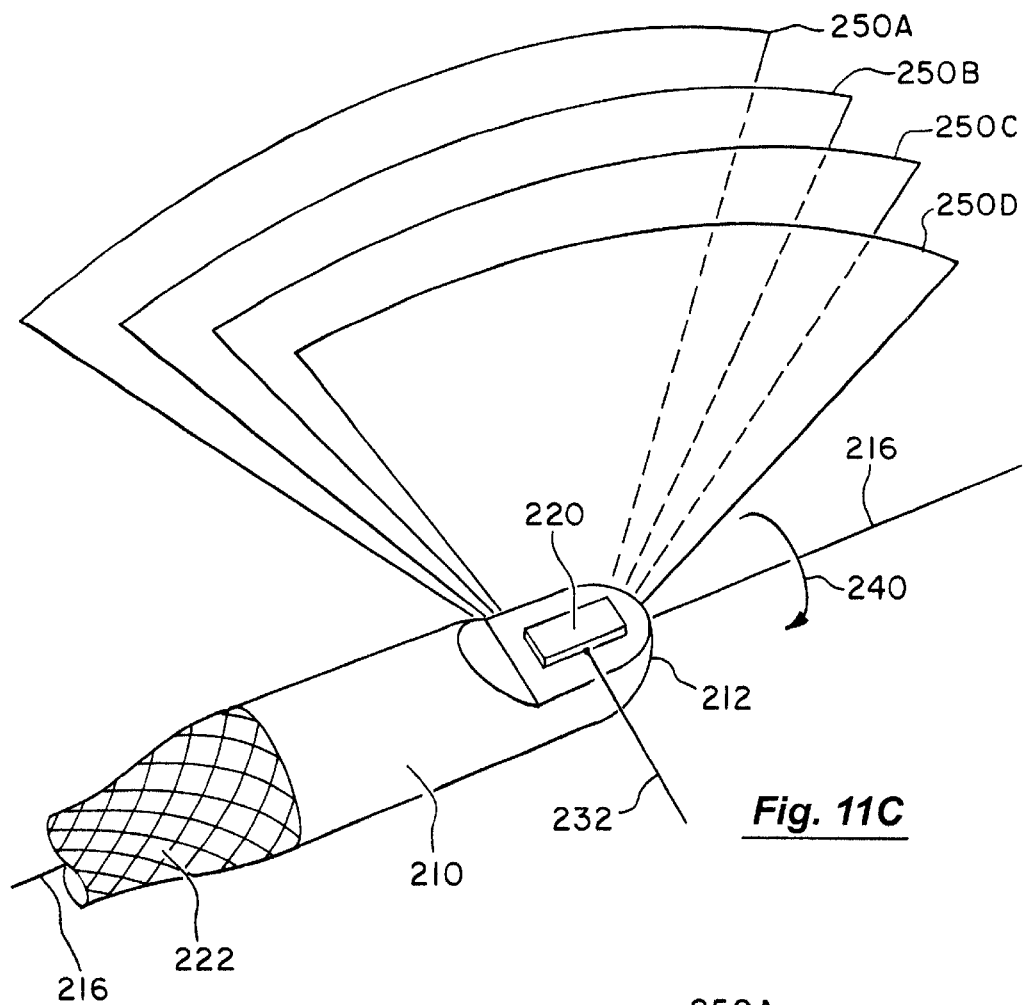
FIGS. 11C–11D depict three-dimensional imaging methods according to the present invention.

As shown in FIG. 11C, the present invention further provides exemplary methods for imaging in a three-dimensional imaging region. As described in conjunction with earlier Figures, transducer 220 is adapted to rotate about an axis of rotation 232 that is at an angle relative to longitudinal axis 216. For example, axis 232 is depicted in FIG. 11C as being generally perpendicular to axis 216. While transducer 220 is depicted as a single rectangular transducer, transducer 220 may have a wide range of shapes and may comprise more than one transducer element within the scope of the present invention. Absent rotation of drive cable 222, transducer 220 projects ultrasound signals into, and receives signals from, a single imaging plane such as plane 250A. In the example shown, plane 250A is not a full 360 degree imaging plane, and is generated, for example, by an angular rotation of transducer 220 about axis 232 that is less than 180 degrees. In other words, plane 250A is imaged by a wiper-like or teeter-totter rotation of transducer 220. Alternatively, rotation of transducer 220 through an angular displacement from +90 degrees to −90 degrees, or through 360 degrees, would produce a larger image plane 250A.

In addition, and as discussed in conjunction with FIGS. 11A–11B, drive cable 222 rotation (shown by an arrow 240) results in transducer 220 rotation about longitudinal axis 216. Typically, drive cable 222 rotation is a continuous 360 degree rotation.

By simultaneously rotating transducer 220 relative to distal end 212, energizing transducer 220, and rotating drive cable 222, the imaging plane for transducer 220 also rotates. As a result, a plurality of imaging planes 250A–250D are imaged by transducer 220. In other words, rotation of transducer 220 relative to distal end images a single plane, such as plane 250A. Rotation of drive cable 222 results in different planes, such as planes 250B–D, being imaged. In this manner, a three-dimensional region is imaged. Controller 150 (FIG. 9) then produces a three-dimensional image of at least a portion of the three-dimensional region.

For methods wherein transducer 220 is rotated through an angular displacement of less than 180 degrees about axis 232, the three dimensional region imaged is generally cone-shaped, hour glass-shaped, or shaped similar to a folded fan. In other methods, the three-dimensional region imaged is generally cylindrical or spherical.

Figure 11D:
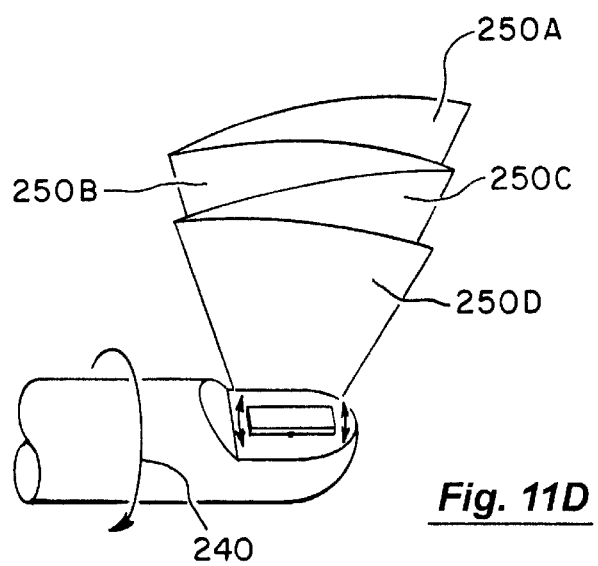

In one preferred embodiment, as shown in FIG. 11C, transducer 220 is rotated relative to distal end 212 at an angular rate of rotation that is greater than an angular rate of rotation of drive cable 222. In this manner, transducer 220 projects ultrasound signals into and receives signals from image plane 250A before doing the same with subsequent image planes 250B–250D. While FIG. 11C depicts distinct image planes 250A–D with gaps therebetween, it will be appreciated by those skilled in the art that rotating transducer 220 at a rate of rotation sufficiently faster than drive cable 222 rotation reduces or eliminates the gaps between planes 250A–D shown in FIG. 11C. Further, the region imaged may comprise a generally spiral-shaped, or folded-fan shaped region, such as that depicted in FIG. 11D. In this manner, a three-dimensional region is imaged.

In an alternative embodiment, the angular rate of rotation of drive cable 222 is greater than the rate of rotation of transducer 220 relative to distal end 212. In this manner, the imaging region can be described as a series of generally parallel imaging planes positioned at right angles to the imaging planes 250A–D depicted in FIG. 11C. For example, transducer 220 may first image the distal-most, 360 degree imaging plane, and continuously image imaging planes more proximal than the previous imaging plane. Depending upon the relative rotations of transducer 220 about axis 232 and drive cable 222 about axis 216, transducer 220 images a spiral-shaped imaging region. In either event, transducer 220 images a three-dimensional region and controller 150 produces a three-dimensional image thereof.

Figure 12:
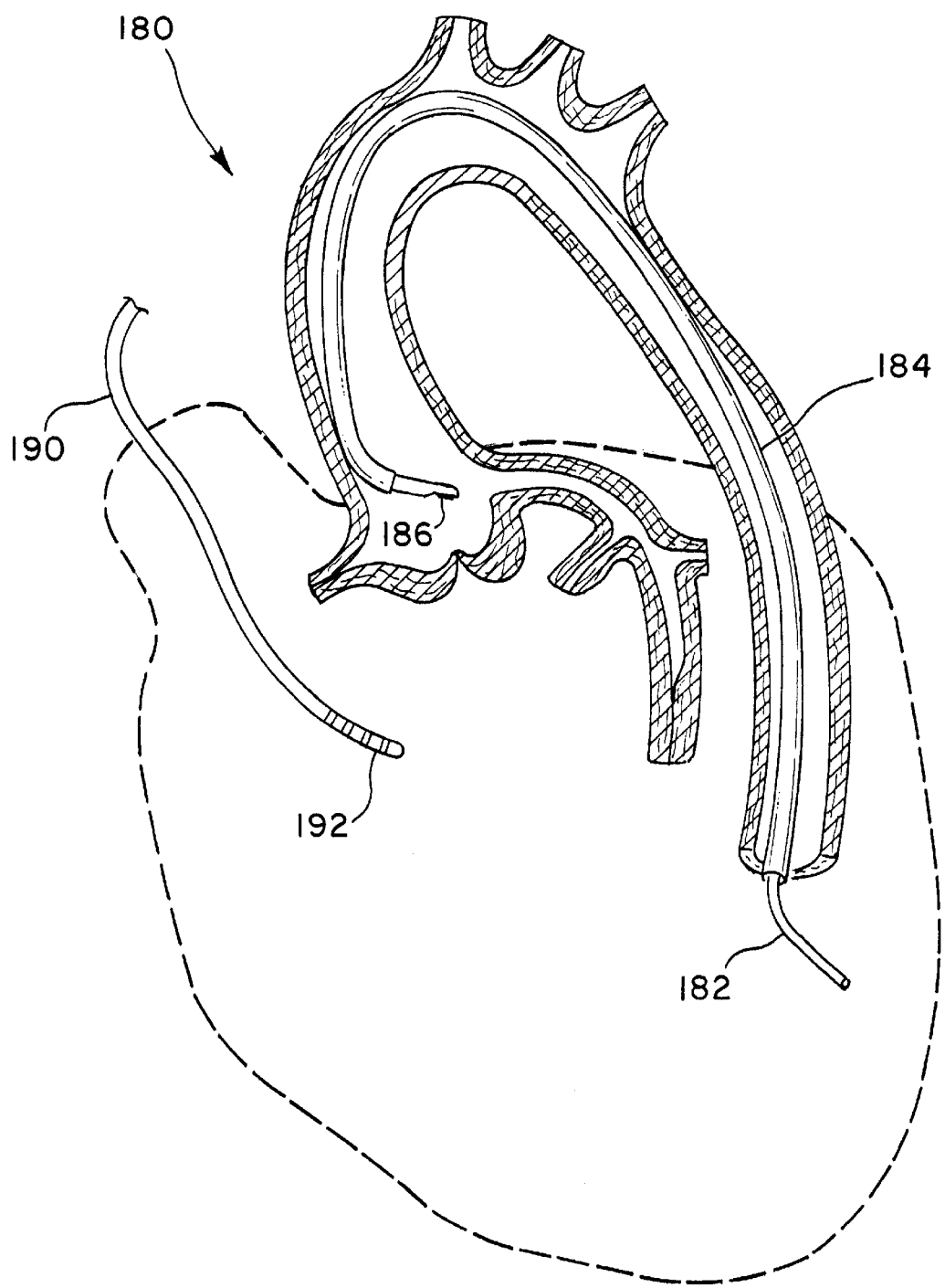
FIG. 12 depicts imaging and ablation catheters positioned inside a patient heart.

FIG. 12 depicts a human heart 180 showing an imaging catheter 182 and an ablation catheter 190 within heart 180. Ablation catheter 190 has a plurality of ablation elements 192 disposed at a distal end. Ablation catheter 190 typically is part of a separate ablation system having a controller and power source similar to, but distinct from controller 150. Ablation elements 192 are positioned within the human heart to ablate cardiac tissue, as may be required to treat atrial fibrillation. Imaging catheter 182 may be inserted into the heart using a guide catheter or sheath 184. Imaging catheter 182 has a transducer 186 at the distal end as described in conjunction with earlier Figures. As can be seen by the positions of catheter 182 and catheter 190, transducer 186 is aligned to provide an imaging plane in the direction of ablation elements 192. Such a configuration will be useful for determining the proper positioning of ablation elements 192.

Another method of using catheters and systems of the present invention involves providing an imaging catheter as previously described. The imaging catheter is inserted into a patient and the transducer or transducer array is positioned at a desired location within the patient. The transducer is rotated about an axis of rotation that is at an angle relative to the catheter body longitudinal axis. The transducer is energized and a plurality of ultrasound signals are propagated into an image plane. A plurality of reflected signals are captured, and an image of at least a portion of the desired location is produced based on the reflected signals.

One of the many benefits of the present invention includes the ability to provide three-dimensional images with a single transducer or a single array of transducers. This is accomplished, in part, by the ability to rotate or translate the single transducer or array in one direction by rotating the catheter distal end, and by rotating the same transducer or array in a second direction relative to the distal end. One method of the present invention permits imaging by a single transducer or array into two different image planes without the need to axially translate the catheter. Further, by providing a three dimensional imaging capability with a single transducer or transducer array in accordance with the present invention, fewer wires are needed to connect the transducer or array to image processing equipment maintained outside the patient. Having fewer wires extending from the distal end to the catheter proximal end permits the use of catheter bodies having smaller diameters. As a result, the catheter can be disposed in smaller arteries, veins and body lumens. The present invention provides these and other advantages over catheters which may have more than one array, or have a comparatively larger number of transducer elements located at the distal end.

The invention has now been described in detail. However, it will be appreciated that certain changes and modifications may be made. For example, descriptions of the operation of imaging catheters of the present invention with respect to an annular array of transducer elements also applies to imaging catheters having a other types of arrays or a single transducer element. Therefore, the scope and content of this invention are not limited by the foregoing description. Rather, the scope and content are to be defined by the following claims.

What is claimed is:

1. An imaging catheter, comprising:
    a catheter body having a distal end, a proximal end and a longitudinal axis; and
    a transducer rotatably coupled to said catheter body distal end, said transducer having an axis of rotation that is at a non-zero angle relative to said longitudinal axis.

2. An imaging catheter as in claim 1, wherein said axis of rotation is generally perpendicular to said longitudinal axis.

3. An imaging catheter as in claim 1, wherein said catheter body has a diameter that is less than about 16 French.

4. An imaging catheter as in claim 1, wherein said transducer comprises a material selected from a group of materials consisting of piezoceramics, piezoplastics and piezocomposites.

5. An imaging catheter as in claim 1, wherein said transducer is rotatably coupled to said distal end to permit 360 degree rotation of said transducer about said rotational axis relative to said distal end.

6. An imaging catheter, comprising:
    a catheter body having a distal end, a proximal end and a longitudinal axis; and
    a transducer rotatably coupled to said catheter body distal end, said transducer having an axis of rotation that is different from said longitudinal axis;
    wherein said transducer is rotatably coupled to said distal end to permit up to about 180 degree rotation of said transducer about said rotational axis relative to said distal end.

7. An imaging catheter as in claim 1, wherein said transducer defines a face that is generally elliptical in shape.

8. An imaging catheter as in claim 7, wherein said face has a major-axis length that is greater than a diameter of said catheter body.

9. An imaging catheter as in claim 1, wherein said transducer comprises an annular array of transducer elements.

10. An imaging catheter as in claim 9, wherein said annular array defines a face that is generally elliptical in shape.

11. An imaging catheter as in claim 10, wherein said face is generally flat.

12. An imaging catheter as in claim 10, wherein said face has a spherical curvature.

13. An imaging catheter as in claim 9, wherein said annular array defines a face that is generally circular in shape.

14. An imaging catheter as in claim 13, wherein said face is generally flat.

15. An imaging catheter as in claim 13, wherein said face has a spherical curvature.

16. An imaging catheter as in claim 1, further comprising a drive cable and a gear mechanism disposed within a working lumen of said catheter body, said drive cable being coupled to said transducer and to said gear mechanism, said drive cable and said gear mechanism being adapted to rotate said transducer.

17. An imaging catheter as in claim 1, further comprising a housing rotatably coupled to said distal end, said transducer being mounted within said housing.

18. An imaging catheter as in claim 1, further comprising a housing operably attached to said distal end, said transducer being rotatably coupled to said housing.

19. An imaging catheter, comprising:
    a catheter body having a distal end, a proximal end and a longitudinal axis; and
    a plurality of transducers configured in an annular array, said annular array being rotatably coupled to said distal end and having an axis of rotation that is at a non-zero angle relative to said longitudinal axis.

20. An imaging catheter as in claim 19, wherein said axis of rotation is generally perpendicular to said longitudinal axis.

21. An imaging catheter, comprising:
    a catheter body having a distal end, a proximal end and a longitudinal axis; and
    a transducer rotatably coupled to said catheter body distal end to permit up to about 180 degrees of rotation, said transducer having an axis of rotation that is not coaxial with said catheter body longitudinal axis.

22. An imaging catheter as in claim 21, wherein said transducer defines a face that is generally parallel to said longitudinal axis during a period of non-rotation.

23. An imaging catheter as in claim 22, wherein said transducer is adapted to rotate so that said face creates an angle with said longitudinal axis that is between about +90 degrees and about −90 degrees.

24. An imaging catheter as in claim 21, wherein said transducer axis of rotation is generally perpendicular to said catheter body longitudinal axis.

25. An imaging catheter system, comprising:
    an imaging catheter comprising,
        a catheter body having a distal end, a proximal end and a longitudinal axis; and
        a transducer rotatably coupled to said catheter body distal end, said transducer having an axis of rotation that is at a non-zero degree angle relative to said longitudinal axis; and a controller operably attached to said imaging catheter to display ultrasound images from signals received from said transducer and to provide power to said imaging catheter.

26. A method of imaging a body lumen, comprising the steps of:
providing an imaging catheter comprising a catheter body having a distal end, a proximal end, a longitudinal axis and a transducer coupled to said distal end;
inserting said imaging catheter into a patient;
positioning said transducer at a desired location within said patient;
rotating said transducer about an axis of rotation that is at a non-zero angle relative to said longitudinal axis;
energizing said transducer;
capturing a plurality of reflected signals; and
producing an image of at least a portion of said desired location based on said reflected signals.

27. A method as in claim 26, wherein said positioning step comprises positioning said transducer at said desired location within the patient's heart.

28. A method as in claim 26, wherein said providing step comprises providing a catheter body having a diameter that is less than about 16 French.

29. A method as in claim 26, wherein said providing step comprises providing said catheter with a plurality of transducers configured in an annular array, said annular array being rotatably coupled to said distal end and having an axis of rotation that is at a non-zero angle relative to said longitudinal axis.

30. A method as in claim 26, wherein said energizing step comprises energizing said transducer to project a plurality of ultrasound signals into an imaging plane.

31. A method as in claim 30, wherein said imaging plane is generally parallel to said longitudinal axis.

32. A method as in claim 30, further comprising coordinating said energizing step and said rotating step to project said plurality of ultrasound signals into a sector of said imaging plane.

33. A method as in claim 30, further comprising coordinating said energizing step and said rotating step to project said plurality of ultrasound signals into a 360 degree sector of said imaging plane.

34. A method as in claim 33, wherein said producing step comprises producing said image of a portion of said imaging plane.

35. A method of imaging a body lumen, comprising:
providing an imaging catheter comprising a catheter body having a distal end, a proximal end, a longitudinal axis and a transducer coupled to said distal end;
inserting said imaging catheter into a patient;
positioning said transducer at a desired location within said patient;
rotating said transducer about an axis of rotation that is at a non-zero angle relative to said longitudinal axis;
energizing said transducer;
capturing a plurality of reflected signals; and
producing an image of at least a portion of said desired location based on said reflected signals;
wherein said rotating step comprises rotating said transducer through an angular displacement that is less than about 180 degrees.

36. A method of imaging a body lumen, comprising:
providing an imaging catheter comprising a catheter body having a distal end, a proximal end, a longitudinal axis and a transducer coupled to said distal end;
inserting said imaging catheter into a patient;
positioning said transducer at a desired location within said patient;
rotating said transducer about an axis of rotation that is at a non-zero angle relative to said longitudinal axis;
energizing said transducer;
capturing a plurality of reflected signals; and
producing an image of at least a portion of said desired location based on said reflected signals;
wherein said providing step comprises providing a transducer that defines a face, said face being generally parallel to said longitudinal axis during a period of non-rotation, and wherein said rotating step comprises rotating said transducer so that said face creates an angle with said longitudinal axis that is between about +90 degrees and about -90 degrees.

37. A method of imaging a body lumen, comprising the steps of:
a) providing an imaging catheter, said catheter comprising,
a catheter body having a distal end, a proximal end and a longitudinal axis; and
a transducer fixedly coupled to said distal end;
b) inserting said imaging catheter into a patient;
c) positioning said transducer at a desired location within said patient;
d) energizing said transducer to project a plurality of ultrasound signals into a first sector of said desired location;
e) capturing a plurality of reflected signals;
f) producing an image of at least a portion of said first sector using said reflected signals;
g) axially translating said transducer within said patient to a second sector of said desired location; and
h) repeating steps (d) through (f) for said second sector.

38. A method as in claim 37, wherein said step (g) comprises axially translating said proximal end a specified distance to axially translate said distal end said specified distance.

39. A method as in claim 37, further comprising combining said image of said first sector and said image of said second sector to produce a three-dimensional image.

40. A method as in claim 37, wherein said energizing step projects said plurality of ultrasound signals into an imaging plane, said imaging plane being generally parallel to said longitudinal axis.

41. A method as in claim 37, wherein said providing step further comprises providing a drive cable and a gear mechanism, said drive cable being coupled to said transducer and to said gear mechanism, said drive cable and said gear mechanism being adapted to axially translate said transducer.

42. A method as in claim 37, further comprising repeating steps (d) through (g) a plurality of times to produce a plurality of images of said desired location.

43. A method as in claim 42, further comprising providing a three-dimensional image of said desired region by combining said plurality of images.

44. A method of imaging a body lumen comprising the steps of:
a) providing an imaging catheter, said catheter comprising,
a catheter body having a distal end, a proximal end and a longitudinal axis;

a transducer coupled to said distal end; and a drive cable coupled to said proximal end;

b) inserting said imaging catheter into a patient;

c) rotating said drive cable to rotate said transducer;

d) energizing said transducer to project a first plurality of ultrasound signals into a first image plane;

e) capturing a first plurality of reflected signals and producing a first image of at least a portion of said first image plane;

f) positioning said transducer at a desired location within said patient;

g) rotating said transducer relative to said distal end and relative to said drive cable;

h) energizing said transducer to project a second plurality of ultrasound signals into a second image plane; and i) capturing a second plurality of reflected signals and producing a second image of at least a portion of said second image plane.

45. A method as in claim 44 wherein said first image plane is generally perpendicular to said longitudinal axis and said second image plane is generally parallel to said longitudinal axis.

46. A method as in claim 44, further comprising repeating steps (d) and (e) until said first image is an image of said desired location.

47. A method as in claim 44, wherein said energizing steps (d) and (h) are performed using the same transducer.

48. A method as in claim 44, wherein said capturing steps (e) and (i) are performed using the same transducer.

49. A method of imaging a body lumen comprising the steps of:

a) providing an imaging catheter, said catheter comprising, a catheter body having a distal end, a proximal end and a longitudinal axis;

a transducer coupled to said distal end; and a drive cable coupled to said proximal end;

b) inserting said imaging catheter into a patient;

c) rotating said transducer relative to said distal end and relative to said drive cable;

d) energizing said transducer to project a plurality of ultrasound signals from said transducer;

e) rotating said drive cable to rotate said transducer;

f) wherein said steps of rotating said transducer, energizing said transducer and rotating said drive cable occur simultaneously to project said plurality of ultrasound signals into a three dimensional imaging region; and g) capturing a plurality of reflected signals from said imaging region and producing a three-dimensional image of at least a portion of said imaging region.

50. A method as in claim 49 wherein said step of rotating said transducer comprises rotating said transducer through an angular displacement that is less than about 180 degrees.

51. A method as in claim 49, wherein said step of rotating said drive cable comprises rotating said drive cable 360 degrees to rotate said transducer 360 degrees.

52. A method as in claim 49, wherein said rotating said transducer step comprises rotating said transducer at a first angular rate of rotation, and wherein said rotating said drive cable step comprises rotating said drive cable at a second angular rate of rotation, said first angular rate of rotation being faster than said second angular rate of rotation.

53. A method as in claim 49, wherein said rotating said transducer step comprises rotating said transducer at a first angular rate of rotation, and wherein said rotating said drive cable step comprises rotating said drive cable at a second angular rate of rotation, said first angular rate of rotation being slower than said second angular rate of rotation.

54. A method as in claim 49, wherein said step of rotating said transducer comprises rotating said transducer about an axis that is generally perpendicular to said longitudinal axis.

55. A method of claim 49, wherein said step of rotating the drive cable rotates the transducer about said longitudinal axis.

* * * * *